United States Patent [19]

Hata et al.

[11] 3,956,276

[45] May 11, 1976

[54] NOVEL ANTIFUGAL ANTIBIOTIC SUBSTANCE, PROCESS FOR PRODUCTION OF THE SAME, AND AGRICULTURAL AND HORTICULTURAL FUNGICIDAL COMPOSITION CONTAINING SAID SUBSTANCE

[75] Inventors: Toju Hata; Satoshi Omura; Michiko Katagiri, all of Tokyo; Juichi Awaya, Soka; Shimpei Kuyama, Tokyo; Shizuo Higashikawa, Kunitachi; Kazuomi Yasui, Hino; Haruko Terada, Hino, all of Japan

[73] Assignees: Nihon Tokushu Moyaku Seizo Kabushiki Kaisha; The Kiyasato Institute, both of Tokyo, Japan

[22] Filed: July 17, 1972

[21] Appl. No.: 272,217

[30] Foreign Application Priority Data
June 29, 1971 Japan..........................46-47411

[52] U.S. Cl............................. 260/211 R; 424/181
[51] Int. Cl.².......................................... C07H 5/00
[58] Field of Search................................ 260/211 R

[56] References Cited
FOREIGN PATENTS OR APPLICATIONS
375,332 4/1964 Switzerland..................... 260/211 R

*Primary Examiner*—Johnnie R. Brown
*Assistant Examiner*—Cary Owens
*Attorney, Agent, or Firm*—Sherman & Shalloway

[57] ABSTRACT

The antifungal antibiotic substance "F-1028" having the following formula,

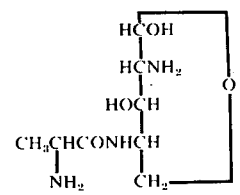

or an acid salt thereof, a process for the production of the same by fermentation, and a fungicidal composition useful for agricultural and horticultural use.

2 Claims, 2 Drawing Figures

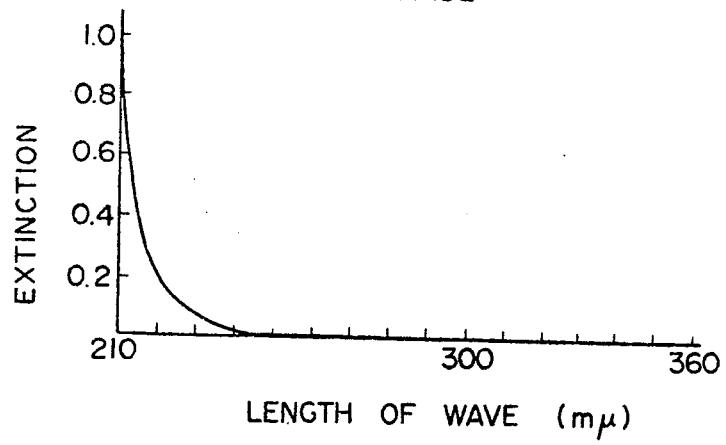
Fig. 1  UV SPECTRUM OF AQUEOUS SOLUTION OF ANTIBIOTIC SUBSTANCE, F-1028 HYDROCHLORIDE
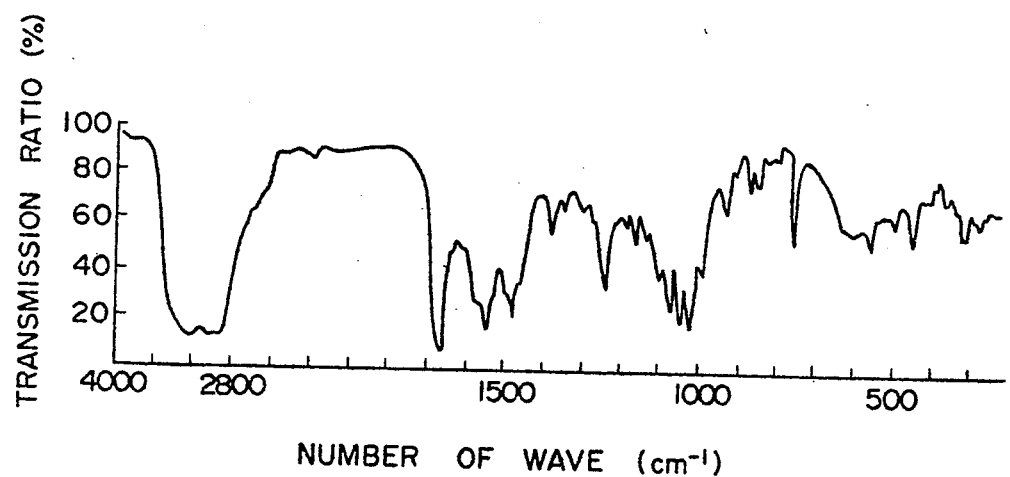
Fig. 2  IR SPECTRUM OF MIXTURE OF F-1028 HYDROCHLORIDE WITH POTASSIUM BROMIDE

NOVEL ANTIFUNGAL ANTIBIOTIC SUBSTANCE, PROCESS FOR PRODUCTION OF THE SAME, AND AGRICULTURAL AND HORTICULTURAL FUNGICIDAL COMPOSITION CONTAINING SAID SUBSTANCE

This invention relates to a novel antifungal antibiotic substance "F-1028" and an acid salt thereof, a process for producing the same by fermentation, and a fungicidal composition useful for agricultural and horticultural use.

We have now found that an antifungal antibiotic substance hitherto unknown can be produced by cultivating "F-1028" substance-producing strain belonging to the genus Streptomyces in a culture medium containing a carbon source, a nitrogen source and a mineral under aerobic conditions.

Before this invention, the existence of a strain belonging to genus Streptomyces which can produce substance "F-1028" having strong antifungal action and growth inhibiting action on various fungi, especially molds, which cause plant diseases was not known.

The novel antifungal antibiotic substance named "F-1028" exhibits strong fungicidal activity against various fungi which cause plant diseases but only weak antibacterial action on various bacteria.

This "F-1028" substance has the following molecular formula

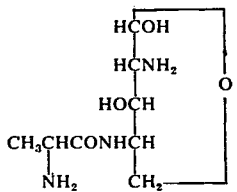

and has the following properties (i) – (ix);
i. it has a molecular weight of 219,
ii. it is colorless crystal,
iii. the melting point of the hydrochloric acid salt thereof is above 195°C (decomposition)
iv. the specific rotation of the hydrochloric acid salt thereof is $[\alpha]_D^{23} = 63.2°$ (c=1, $H_2O$),
v. the UV spectrum of an aqueous solution of the hydrochloric acid salt thereof has no peculiar absorption as shown in FIG. 1,
vi. the IR spectrum of a mixture of the hydrochloric acid salt thereof with potassium bromide is as shown in FIG. 2,
vii. it has an Rf value in thin-layer chromatography with silica gel of 0.68 with a developing solvent consisting of n-propanol-pyridine-acetic acid-water in a ratio of 15:10:3:12; and 0.21 with a developing solvent consisting of butanol acetic acid-water in a ratio of 3:1:2,
viii. it is readily soluble in water and insoluble in chloroform, benzene and ether, and
ix. the color reaction is positive with ninhydrin, Ehrlich, Elson-Morgan, Tollens and Benedict reagents, and negative with Molisch, Sakaguchi, maltol and ferric chloride reagents.

This "F-1028" substance has activity against Archimycetes, Phycomycetes, Ascomycetes, Basidiomycetes, and *Fungi imperfecti*. It can be used for example as a plant-protecting fungicide having both preventive and curative effects against a wide variety of plant pathogens causing such diseases as blast, sheath blight, bacterial leaf blight, or helminthosporium leaf spot of rice, leaf rust of wheat, bacterial soft rot of Chinese cabbage, brown rot of peach, leaf spot of banana, gray mold of strawberry and other crops, downy mildew of grape, anthracnose of grape, apple and pear, stem rot of vegetables, anthracnose of melons and cucumber, melanose of citrus fruits, powdery mildew of wheat, apple, and cucumber, fungi causing black spot, for example, brown spot disease on apple or early blight on potato, fungi causing scab, for example, scab on pear or apple.

The present inventors newly separated the "F-1028" substance-producing strain from soil and named it *Streptomyces kagawaensis*.

The *Streptomyces kagawaensis* nov. sp. (FERM-P No. 953: ATCC No. 21811) is characterized by the following microbiological properties.

I. Morphological properties:

According to the microscopic observation, the aerial mycelium on a synthetic agar medium and a protein agar medium is branched irregularly. Sporangiopere forms closed spirals with no whorl. Spore is ellipse in size of $0.7\mu \times 0.9\mu$ and has spinous surface.

II. Cultural characteristics on various culture media:
 1. Sucrose-nitrate agar medium (at 27°C).
     Growth; Good, pale yellowish brown to light pale yellow.
     Aerial mycelium; Powdery, abundant, grayish brown.
     Reverse; Yellow.
     Soluble pigment; Pale brown.
 2. Glucose-asparagin agar medium (at 27°C).
     Growth; Good, pale yellow to pale yellowish brown.
     Aerial mycelium; Powdery, abundant, pale pink to brownish white.
     Reverse; Yellowish brown.
     Soluble pigment; Pale yellow.
 3. Glycerin-asparagin agar medium (at 27°C).
     Growth; Good, yellowish brown, vegetative mycelium enters into the medium.
     Aerial mycelium; White to pinkish white.
     Reverse; Brown.
     Soluble pigment; Yellowish brown.
 4. Starch-inorganic salt agar medium (at 27°C).
     Growth; Good, pale yellow.
     Aerial mycelium; Powdery, brownish white to pale brown.
     Reverse; Yellowish brown.
     Soluble pigment; Yellowish brown.
 5. Thyrosine agar medium (at 27°C).
     Growth; Light yellowish brown to dark brown.
     Aerial mycelium; White to brownish white.
     Reverse; Brown to dark brown.
     Soluble pigment; Black.
 6. Nutrition agar medium (at 27°C).
     Growth; Light yellowish brown.
     Aerial mycelium; None.
     Reverse; Brown.
     Soluble pigment; Yellowish brown.
 7. Yeast-malt agar medium (at 27°C).
     Growth; Good, yellowish brown, vegetative mycelium enters into the medium.
     Aerial mycelium; Cotton like, white to pale pink.
     Reverse; Brown.
     Soluble pigment; Yellowish brown.

8. Oat meal agar medium (at 27°C).
   Growth; Good, yellowish brown, vegetative mycelium enters into the medium.
   Aerial mycelium; Powdery, abundant, bright brown.
   Reverse; Brown.
   Soluble pigment; Yellowish brown.
9. Peptone-yeast iron agar medium (at 27°C).
   Growth; Lustrous yellowish white.
   Aerial mycelium; None.
   Reverse; Grayish brown.
   Soluble pigment; Dark brown.
10. Loeffler coagulated serum agar medium (at 27°C).
    Growth; Lustrous brown.
    Aerial mycelium; Scant, white.
    Soluble pigment; Brown, no liquefaction.
11. Egg agar medium (at 27°C).
    Growth; Creased, yellowish brown to dark brown.
    Aerial mycelium; White to dim white.
    Reverse; Brownish brown.
    Soluble pigment; Dark yellowish brown, no liquefaction.
12. Potato plug (at 27°C).
    Growth; Thick, raised lustrous yellowish brown.
    Aerial mycelium; Scant, white.
    Soluble pigment; Yellowish brown to dark brown.
13. Carrot plug.
    Growth; Thick, raised, lustrous yellowish brown.
    Aerial mycelium; Cotton like, white.
    Soluble pigment; Scant, pale yellowish brown.
14. Glucose-peptone gelatin medium (at 27°C).
    Growth; Creased, pale grayish brown.
    Aerial mycelium; Pale grayish white.
    Soluble pigment; Brown.
15. Skim milk medium (at 27°C).
    Growth; Ring or membrane, pale yellowish brown.
    Aerial mycelium; Scant, white.
    Soluble pigment; Pale yellowish brown.
III. Physiological properties:
1. Optimum conditions for growth:
   Temperature: between 25° to 30°C.
   pH: between 6 to 8.
   Aerobic condition.
2. Growable conditions:
   Temperature: between 15° to 38°C.
   pH: between 4 to 9.
3. Formation of melanine: positive.
4. Reduction of nitric acid: weak.
5. Milk coagulation: weak.
6. Milk-peptonization: moderate.
7. Gelatin-liquefaction: weak.
8. Decomposition of starch: positive.
9. Formation of hydrogen sulfide: positive.
10. Dissolution of coagulated serum: negative.
IV. Assimilation of carbon sources:
The assimilation of carbon sources was tested by the method of D. G. Pridham et al.
Good assimilation:
  Arabinose, glucose, galactose, glycerol, levulose, mannose, maltose, melibiose, sucrose, trehalose, inositol, mannitol.
Moderate assimilation:
  Lactose, xylose.
Slight assimilation:
  Raffinose, rhamnose, salicin, inulin, sorbinol.
No assimilation:
  Melezitose, sorbose, adonitol, dulcitol.

According to these microbiological properties, the "F-1028" substance-producing strain, which grows with pale pink or grayish brown aerial mycelium and produces a brown or yellowish brown soluble pigment on a protein agar medium, is considered to below to Strepromyces, particularly *Streptomyces lavendulae*.

Among known species of Streptomyces having these characteristic properties, *Streptomyces lavendulae*, *Streptomyces venezuelae* and *Streptomyces verginiae*, described in Bergey's Manual of Determinative Bacteriology, 7th ed. and the Actimomycetes by Waksman, Vol. 2, are similar to the strain of this invention.

However, the spore surfaces of these three strains are smooth, but on the contrary, that of the "F-1028" substance-producing strain is spinous. Comparison of the cultural properties between the "F-1028" substance-producing strain and these three strains shows that the three strains produce no soluble pigment but the "F-1028" substance-producing strain produces yellowish brown soluble pigment on sucrose-nitrate agar medium. Also, in the assimilation of carbon sources, any of these three strains shows little or no assimilation of merbiose, sucrose, inositol and mannitol, but the "F-1028 substance-producing strain assimilates these saccharides well.

By the differences of the morphological, cultural and physiological properties, the "F-1028" substance-producing strain can be clearly distinguished from *Streptomyces lavendulae*, *Streptomyces venezuelae* and *Streptomyces verginia*. The present inventors classified the "F-1028" substance-producing strain as *Streptomyces lavendulae* group in view of the cultural and physiological properties, but distinguished it as a new strain from the known microorganisms under the name of *Streptomyces kagawaensis* nov. sp., according to the differences of spore surface structure and saccharide-assimilation and the possibility of producing a new antibiotic "F-1028" substance.

*Streptomyces kagawaensis* is easily converted to a mutant strain by means of artificial mutations such as application of an ultraviolet ray, X-rays, or a high frequency wave, or radial rays, chemicals.

In the process of the present invention, there are employed all strains, which have a productivity of "F-1028" substance, including mutants of a standard strain which are not clearly distinguished from *Streptomyces kagawaensis* as a standard strain.

The important aspect of the process of the present invention is based on the steps of culturing the "F-1028" substance-producing strain belonging to *Streptomyces kagawaensis* and isolating the antibiotic "F-1028" substance from the culture medium.

In this invention, the "F-1028" substance-producing strain is cultured in a culture medium containing nutrients utilized by general microorganisms. As the nutrient source, all of the known nutrients for actinonyces can be used, for example, commercially available glucose, starch, glycerol, sucrose, maltose, dextrin, molasses and fats as carbon sources (shown in Table 1).

Examples of the nitrogen source are commercially available soybean flour, meat extract, peptone, yeast, corn steep liquor, powdered cotton seed, powdered peanut, N-Z amine, casein, ammonium sulfate, ammonium nitrate and sodium nitrate (shown in Table 2).

Examples of the minerals (or inorganic salts) are calcium carbonate, sodium chloride, potassium chloride, phosphate, magnesium sulfate. If desired, a trace amount of metallic salts can be incorporated.

Any substance of these nutrients may be used, if it is assimilated by the "F-1028" substance-producing strain and useful for producing the "F-1028" substance.

Production of the "F-1028" substance in a culture medium containing various carbon sources will now be described.

In a test tube (20 mm in diameter) was placed 13 ml of a liquid culture medium containing a basic medium, which consisted of peptone 0.5%, meat extract 0.5%, dried yeast 0.3%, sodium chloride 0.5% and calcium carbonate 0.3%, and the carbon sources described in the following table (shown in Table 1). Then the seed culture of the "F-1028" substance-producing strain was inoculated to the culture medium. The inoculated test tube was incubated with shaking in a reciprocated shaker at 27°C. The production of the "F-1028" substance is shown in Table 1.

Table 1

| | Carbon source | | Two days pH | F-1028 mcg/ml | Three days pH | F-1028 mcg/ml |
|---|---|---|---|---|---|---|
| 1 | Glucose | 2.0 % | 7.4 | 632 | 7.6 | 280 |
| 2 | Glycerol | 2.0 % | 7.4 | 452 | 7.4 | 258 |
| 3 | Starch | 2.0 % | 7.6 | 548 | 8.0 | 148 |
| 4 | Glucose | 1.0 % | 7.4 | 538 | 8.0 | 184 |
| | Starch | 1.0 % | | | | |
| 5 | Glycerol | 1.0 % | 7.6 | 590 | 8.0 | 210 |
| | Starch | 1.0 % | | | | |
| 6 | Maltose | 2.0 % | 8.2 | 78 | 8.4 | 32 |
| 7 | Dextrin | 2.0 % | 7.8 | 284 | 7.8 | 420 |
| 8 | Sucrose | 2.0 % | 8.4 | 36 | 8.4 | |

Production of the "F-1028" substance in a culture medium containing various nitrogen sources will now be described.

To a basic medium consisting of glucose 2.0%, sodium chloride 0.5%, calcium carbonate 0.3%, the nitrogen sources as shown in the following table were added. The culture medium was adjusted to pH 7, sterilized, inoculated with the seed culture of the "F-1028" substance-producing strain and shaken at 27°C. The production of the "F-1028" substance is described in Table 2.

Table 2

| | Nitrogen source | | Two days pH | F-1028 mcg/ml | Three days pH | F-1028 mcg/ml |
|---|---|---|---|---|---|---|
| 1 | Peptone | 1.0 % | 7.6 | 632 | 7.8 | 420 |
| 2 | Meat extract | 1.0 % | 7.8 | 1212 | 7.8 | 358 |
| 3 | Powdered soybean | 3.0 % | 7.4 | 580 | 7.8 | 322 |
| 4 | Corn steep liquor | 2.0 % | 7.4 | 368 | 7.8 | 174 |
| 5 | Dried yeast | 1.0 % | 6.8 | — | 6.4 | 116 |
| 6 | Peptone Meat-extract Dried yeast | 0.5 % 0.5 % | 7.6 | 322 | 7.8 | 342 |

The best cultural method uses a liquid culture, expecially a submerged tank culture with aeration at temperatures ranging over the extent in which the "F-1028" substance-producing strain is growable and produces the "F-1028" substance, preferably at 25° to 35°C. The practical culture is conducted at about 27°C and continued until the "F-1028" substance is sufficiently accumulated. The pH value of the cultural medium is usually from 6 to 9, preferably 6.2 to 8.5, especially 6.5 to 8. The concentration of the "F-1028" substance in the culture medium becomes maximum within 2 to 5 days by both shaking culture and tank culture method. However, since the days needed to get the maximum concentration of the "F-1028" substance may be varied in accordance with condition of aeration and agitation in the same culture medium at the same temperature, it is desirable to determine the potency of the "F-1028" substance. When the potency is maximum, the culture is stopped and the "F-1028" substance is extracted. To determine the potency of the "F-1028" substance, there was employed a method of measuring an inhibition circle by using Sclerotinia cinerea (hereinafter referred to as Sc) in accordance with a conventional way.

The practice was conducted as follows:

One Kg of potato and 15 lit. of tap water were boiled for 30 minutes and the potatos were filtered away by gauze. Then to the filtrate, water was added in an amount of 5 lit. and commercially available sucrose was incorporated at 2% to prepare a culture medium for Sc. To this liquid medium agar was added at 1.5% and it was placed in a test tube in order to make a slant culture medium. Sclerotinia cinerea strain was inoculated on the slant medium and incubated for 4 to 7 days at 27°C and 2 or 3 loopful of Sc strain on the slant culture medium were inoculated in 100 ml of Sc culture medium containing agar at 0.3% in a Sakaguchi's flask. After the flask was shaken for 4 days at 27°C, the cultivated medium was homogenized for 2 minutes at 9,000 r.p.m. It was used then for seeding. Thereafter, 10 ml of the Sc liquid medium added agar at 1 to 1.2% was placed in a petri dish, solidified and covered with 4 ml of the same agar medium mixed with the cultivated medium at 10%. This plate culture medium was used in a conventional disc method. The culture was continued for 2 days at 27°C. In this method, a 200 mcg/ml solution of the pure "F-1028" substance forms an inhibition zone with about 35 mm diameter. A linear relationship between the concentration of the antibiotic and the diameters of inhibition zones stands at a range 10 to 200 mcg/ml.

Since the "F-1028" substance has physical and chemical properties as described hereinafter, the substance can be extracted and purified in accordance with the properties. The "F-1028" substance was produced in the culture liquid, the mycelia are removed away by methods of centrifuging or filtration with auxiliary filters such as kieselguhr at acidity or neutrality. Then the "F-1028" substance was adsorbed on a cation exchange resin, for example IRC-50($Na^+$) or IR-120($H^+$), by the batch or column method, and eluted with acidic or basic water. The "F-1028" substance is a strong basic compound which is not substantially adsorbed on IRC-50($H^+$), but it is adsorbed on the resin in $Na^+$ type. For instance, the filtrate of the fermentation mixture is treated with oxalic acid, and adsorbed on IRC-50($Na^+$), and the antibiotic was eluted rapidly with 1 N-HCL. In the case of using activated carbon, the "F-1028" substance can be adsorbed on the carbon and eluted with aqueous acetone and aqueous methanol but not substantially.

After the eluate containing the "F-1028" substance was concentrated under reduced pressure, the concentrate, if necessary, was desalted with methanol, ethanol and added with an exessive amount of methanol ethanol and acetone to precipitate the "F-1028" substance in the form of powder. The eluate from the resin decomposed easily with coloring in brown by drying directly under reduced pressure. It was necessary to treat the "F-1028" substance rapidly, because its activity became lower and it coloured in yellow when it was allowed to stand for a long time. The mixture containing the "F-1028" substance was decomposed in brown by precipitation with methanol, ethanol and acetone and drying. However, the "F-1028" substance is very stable as far as it is in the form of aqueous solution. The crude powder obtained was purified by methods such as carbon chromatography or Sephadex chromatography to obtain a white powder.

The eluate as hydrochloride was then passed through a column of IR-4B resin to be converted to a free type and thereafter to a sulfate by eluting with sulfuric acid. In this case, if the amount of IR-4B resin was not sufficient and the eluates from IR-4B resin were passed through a column of Sephadex G-10, two fractions were eluted from the Sephadex column. The first fraction was a sulfate of the "F-1028" substance and the second was a hydrochloride. The latter fraction was again passed through the column of IR-4B resin and eluted with sulfuric acid and the eluate was subjected to the Sephadex column to form a sulfate. The "F-1028" substance isolated and purified by the methods described above, has the following more detailed physical and chemical properties.

1. Colorless needle-like or plate-like crystal.
2. Melting point (hydrochloride), decomposed at above 195°C.
3. Elemental analysis (as hydrochloride):
   Found: C: 30.94%, H: 6.58%, N: 13.39%, O: 25.91%, Cl: 23.18%.
4. Molecular formula: $C_8H_{17}N_3O_4$. (molecular weight: 219, from elemental analysis, titration and NMR spectrum).
5. Equivalent: 122.5 (from titration).
6. Specific rotation (hydrochloride):
   $[\alpha]_D^{23} = 63.2°$ (C=1, $H_2O$).
7. PKa': 7.02 and 8.16.
8. Ultraviolet absorption spectrum:
   No peculiar absorption as shown in FIG. 1.
9. Infrared absorption spectrum:
   As shown in FIG. 2.
10. Rf value:
    When a thin layer chromatography based on silica gel is used with a developing solvent consisting of butanol, acetic acid and water in a ratio 3:1:2, Rf value is 0.25. When the solvent consists of n-propanol, pyridine, acetic acid and water in a ratio of 15:10:3:12, Rf value is 0.68.
11. Solubility:
    Readily soluble in water;
    Soluble in methanol and dimethyl sulfoxide;
    sparingly soluble in ethanol;
    Insoluble in chloroform, benzene and ether.
12. Color reaction:
    Positive: Ninhydrin, Ehrlich, Elson-Morgan, Tollens, and Benedict reactions.
    Negative: Molisch, Sakaguchi, maltol, and ferric chloride reactions.
13. It retains its activity in an acidic solution, but the activity is reduced when the solution becomes neutral to alkaline.

Biological properties of the "F-1028" substance
1. Antimicrobial activity:
   The minimum inhibitory concentration (MIC) of the "F-1028" substance for various microorganisms was examined by the agar dilution method, and the results are given in Table 3.

Table 3

| Microorganism | 24 hours mcg/ml | 48 hours mcg/ml |
|---|---|---|
| Staphylococcus aureus FDA 209 p | >100 | >100 |
| Sarcina lutea PCI 1001 | 3.12 | 3.12 |
| Bacillus subtilis PCI 219 | >100 | >100 |
| Mycobacterium ATCC 607 | >100 | >100 |
| Escherichia coli NIHJ | 100 | >100 |
| Vibrio comma 904 | 12.5 | 100 |
| | 48 hours | 72 hours |
| Candida albicans | >100 | >100 |
| Saccharomyces cerevisiae | >100 | >100 |
| Holmodendrum pedrosei | 25 | 25 |
| Trichophyton rubrum | 100 | >100 |
| Ophiobolus miyabianus | 25 | 25 |
| Aspergillus niger | >100 | >100 |
| Xanthomonas oryzae | 50 | 100 |
| Xanthomonas citri | >100 | >100 |
| Alternaria japonica | 50 | 50 |
| Alternaria kikuchiana | >100 | >100 |
| Sclerotinia cinerea | 12.5 | 25 |
| Sclerotinia sclerotiorum | 1.56 | 3.12 |
| Botorytis fabae | 6.25 | 25 |
| Botorytis cinerea | 6.25 | 12.5 |

Toxicity
i. No abnormality.
   Mice (intravenous injection) 125 mg/kg, (oral administration) 500 mg/kg.
   Young carp: no trouble with 250 ppm
ii. Mice (intravenous injection) $LD_{50}$, 160 mg/kg, (oral administration) $LD_{50}$, 750 mg/kg.

Accordingly, the "F-1028" substance has very low toxicity. Since these physiological, chemical and biological properties of the "F-1028" substance do not correspond with those of the known numerous antibiotics, the antibiotic, "F-1028" substance is confirmed to be a new antibiotic substance.

The "F-1028" substance of the invention can be applied effectively to pathogens living on the aboveground portions of plants, pathogens which invade plants from the soil and cause tracheomycosis, seed-infectious pathogens, and soil-infectious pathogens.

As mentioned before, the "F-1028" substance of this invention exhibits superior control effect against pathogens which invade rice plants and other crops, and has good affinity for higher plants. With ordinary dosages, it does not give phytotoxicity to crops, and hardly exhibits toxicity on domestic animals and fish. Thus, this substance can be used against plant pathogens as agricultural and horticultural fungicide quite conveniently, and is practically very valuable for increasing agricultural productivity.

In the application of the "F-1028" substance of this invention as an agricultural and horticultural fungicide, it can be used after dilution with water, or as various formulations prepared by the method usually practised in the field of producing agricultural chemicals using agricultural chemical assistants. These various formulations may be applied as such or after dilution with water to the desired concentrations.

As the agricultural and horiticultural assistants referred to herein, there can be named inert solvents and/or diluents (extenders or carriers) (these are used to carry the active ingredient to pathogenic fungi and/or the habitat of the pathogenic fungi). There can also be cited various surface active agents and/or organic materials, such as stabilizers, spreaders (stickers), propellants for aerosols, or synergizing agents (these are used to produce, maintain, and promote the effect of the active compound to a greater extent).

Examples of the solvent include water, and organic solvents, for example, aliphatic or alicyclic hydrocarbons such as n-hexane, industrial gasolines (petroleum ether, solvent naphtha, etc.), petroleum fractions (paraffin wax, kerosene, light oil, middle oil, heavy oil, etc.), aromatic hydrocarbons such as benzene, toluene, xylenes, or aromatic naphtha, halogenated hydrocarbons such as chloromethylene, chloroethylene, carbon tetrachloride, trichloroethylene, ethylene dibromide, or chlorobenzene, alcohols such as methyl alcohol, ethyl alcohol, propyl alcohol, or ethylene glycol, ethers such as ethyl ether, ethylene oxide, or dioxane, alcohol ethers such as ethylene glycol or monomethyl ether, ketones such as acetone and isophorone, esters such as ethyl acetate or amyl acetate, amides such as dimethyl formamide or dimethyl acetamide, and sulfoxides such as dimethyl sulfoxide.

Examples of the diluents (extenders or carriers) include vegetable powders, mineral powders, clay minerals such as kaolinites, montmorillonites or attapulgites, talc, pyrophyllite, mica, gypsum, calcite, muscovite, vermiculite, dolomite, apatite, slaked lime, magnesium lime, diatomaceous earth, inorganic acid salts such as calcium carbonate, sulfur, pumice, synthetic mineral powders such as highly dispersed silicic acid or synthetic alumina, synthetic resins such as phenolic resins, urea resins, or vinyl chloride resins.

Examples of the surface active agents include anionic surface active agents such as alkylsulfuric acid esters (for example, sodium laurylsulfate), arylsulfonic acids (for example, alkylarylsulfonic acid salts or sodium alkylnaphthalenesulfonate), cationic surface active agents such as alkylamines (for example, laurylamine, stearyl trimethyl ammonium chloride, or alkyl dimethylbenzylammonium chlorides), or polyoxyethylene alkyl amines, non-ionic surface active agents such as polyoxyethylene glycol ethers (for example, polyoxyethylene alkylaryl ethers, or polyoxyethylene alkylphenyl ethers), polyhydric alcohol esters (for example, polyoxyethylene sorbitan monolaurate), or polyoxyethylene glycol esters (for example, polyoxyethylene fatty acid esters), and amphoteric surface active agents.

As the examples of the organic materials, there can be cited stabilizers, spreaders (stickers) such as agricultural soap, coumarone or indene resins, or polyvinyl butyl ether, propellants for aerosols such as halogenated hydrocarbons (Freon, etc.), combustion agents for fumigants, such as nitrous acid salts, zinc powder, or dicyandiamide, oxygen-yielding agents such as perchlorates or bichromates, phytotoxicity-reducing agents such as zinc sulfate, ferrous chloride, or copper nitrate, effect-extending agents such as chlorinated terphenyl, dispersion stabilizers such as casein, tragacanth, carboxymethyl cellulose, or polyvinyl alcohol, and synergizing agents.

The compound of this invention can be prepared into various formulations by the method generally practised in the field of producing agricultural chemicals.

Examples of the formulations are liquid preparations, such as emulsifiable concentrates, wettable powders, tablets, soluble powders, or solutions, dusts, granules, fumigants, or aerosols.

The fungicide of this invention may contain the above active ingredient in an amount of 0.1 to 95% by weight, preferably 0.5 to 90% by weight.

In actual application, the suitable amount of the active ingredient contained in the above-mentioned various formulations or in a ready-to-use preparation is generally from 0.0001 to 20% by weight, preferably from 0.005 to 10% by weight.

The content of the active ingredient may be changed properly according to the formulations, the method, purpose, time, and place of application, and the state of disease occurrence, etc.

If desired, the compound of this invention may further contain other agricultural chemicals such as insecticides, fungicides, acaricides, nematocides, antivirus agents, herbicides, plant growth modifiers, or attractants (for example, organophosphorus esters, carbamates, dithio (or thiol) carbamates, organic chlorides, dinitro compounds, organic sulfur or metal compounds, antibiotics, substituted diphenyl ether compounds, urea compounds, or triazine compounds), and/or fertilizers.

Various formulations or ready-to-use preparations containing the active ingredient of this invention described above can be applied by the method generally practised in the field of agricultural chemicals, such as spraying (for example, liquid preparation spraying, misting, atomizing, dust spraying, granule spraying, application to the water surface, or pouring), fumigating, application to the soil (for example, sprinkling, vaporing, or pouring), application to the surface of the soil (for example, coating, banding, dust application, or covering), or impregnation. They can also be applied by the ultra-low-volume spraying method. According to this method, the active ingredient can be included in an amount of up to 95% or even 100%.

The amount of application per unit area of the fungicide of this invention is about 3–1000 g, preferably 30–600 g, per 10 areas calculated as the active compound. But in special cases, the amount may either be above or below this range, or sometimes, it is even necessary to deviate from this range.

According to this invention, there is provided a fungicidal composition comprising the compound of formula (I) as an active ingredient, and a solvent and/or a diluent (extender or carrier) and/or a surface active agent, and if desired, an organic material.

Furthermore, the present invention provides a method of controlling pathogenic fungi, which comprises applying the compound of formula (I) singly or in admixture with a solvent and/or a diluent (extender or carrier) and/or a surface active agent, and if desired, further with an organic material to said fungi and/or their habitat.

The present invention will be specifically described by the following Examples, but it should be understood that the invention is not limited in any way to these Examples.

FIG. 1 shows a UV spectrum curve of an aqueous solution of the hydrochloride of the antibiotic, the "F-1028" substance, of this invention.

FIG. 2 shows a IR spectrum curve of the hydrochloride of the "F-1028" substance mixed with potassium bromide.

EXAMPLE 1

A loopful micelium of Streptomyces kagawaensis, the "F-1028" substance-producing strain, was inoculated to a cultural medium containing meat extract 0.5%, sodium chloride 0.5%, yeast extract 0.3%, glucose 2%, peptone 0.5% and calcium carbonate. After the inoculated medium was cultivated with shaking for 2 days, it was placed in a 100 lit.-fermentation tank with 75 lit. of the same culture medium. Then this inoculated medium was incubated at 27°C with aeration of 10 lit./min, agitation of 250 r.p.m., and internal pressure of 0.5 kg/cm² for 2 days. The production of the "F-1028" substance then reached 400 mcg/ml. in the broth. 70 lit. of the cultivated medium was adjusted to pH 2 by a saturated solution of oxalic acid and filtered with celite at 0.5%. Then the filtrate was adjusted to pH 5 with 2N-NaOH and stirred together with 2.8 lit. of cation exchange resin, Amberlite IRC-50(Na⁺), for 30 minutes. Successively, the resins were collected by filtration, and the filtrate was adjusted again to pH 5, admixed with 1.4 lit. of Amberlite IRC-50(Na⁺), stirred and filtered. These resins were collected, too. By two of these operations, 95 % of the "F-1028" substance in the filtrate was adsorbed by the resin. Thereafter, the resin which adsorbed the "F-1028" substance was washed sufficiently with water and charged into a column. The "F-1028" substance was eluted with 1N-HCl, and about 5 lit. of the eluate containing the active substance was collected and concentrated to 100 ml under reduced pressure. After the filtration of sodium chloride formed in this step, three-fold quantity of methanol was added to the solution. It was allowed to stand under cold conditions. The sodium chloride further formed was filtered away, ten-fold quantity of acetone was added. Then the precipitate of the "F-1028" substance was formed and 95 g of the "F-1028" substance as crude powder (Yield: 60 to 70%) was obtained by drying the precipitate.

EXAMPLE 2

125 ml of a medium containing glucose 2%, soy-bean meal 3%, sodium chloride 0.5% and calcium carbonate 0.5% were placed in a 500 ml-Sakaguchi's flask sterilized and inoculated by 2 ml of precultivated medium of *Streptomyces kagawaensis*, the "F-1028" substance-producing strain. Then the flasks were incubated at 27°C with shaking at 120 r.p.m. and with 8 cm amplitude. After 48 hours, potency of the "F-1028" substance became 580 mcg/ml. The broth was collected and the active compound was extracted by the same methods as in Example 1 to be a crude powder.

EXAMPLE 3

A mutant of Streptomyces kagawaensis, obtained by treatment with N-methyl-N'-nitro-N-nitrosoguanidine and grew with pink or brownish gray aerial mycelia, was precultured. And the cultivated medium was inoculated by 2 ml in 500 ml-Sakaguchi's flask placed with 125 ml of cultural medium containing glucose 2%, peptone 0.5%, meat extract 0.5%, dried yeast 0.3%, sodium chloride 0.5%, calcium carbonate 0.3%. Then the flasks were incubated at 27°C with shaking at 120 r.p.m. with 8 cm amplitude. By the same procedure as in Example 1, the active compound was extracted to obtain the "F-1028" substance in a crude powder. The results were shown in Table 4.

Table 4

| Strain | 2 days | | 3 days | |
|---|---|---|---|---|
| | pH | F-1028 (mcg/ml) | pH | F-1028 (mcg/ml) |
| Monospore-culturing pinky brown M 1 strain | 8.0 | 1580 | 8.0 | 736 |
| Monospore-culturing pale pink M 2 strain | 8.4 | 2160 | 8.2 | 2220 |
| Nitrosoguanidine-treated brownish gray N 1 strain | 7.2 | 1106 | 7.8 | 474 |
| Nitrosoguanidine-treated white N 2 strain | 6.2 | 452 | 7.6 | 2000 |

Table 4-continued

EXAMPLE 4

6 g of the crude powdered "F-1028" substance, obtained in Example 1 was dissolved in 10 ml of water, adsorbed on a column filled with 60 g of activated carbon for chromatography (produced by Wako Seiyaku Co., Ltd.) and developed with water, and the "F-1028" substance was eluted in a colorless aqueous solution (Yield: 91.5 %). Then the solution was concentrated in vacuo and admixed with about 20-fold quantity of ethanol. The precipitate was dried to obtain 4 g of the crude "F-1028" substance in powder. Successively, 2 g of the powder was dissolved in 4 ml of water, poured into Sephadex G-10 column (2.5 × 150 cm) and developed with water. The active fraction was concentrated in vacuo to obtain 1.15 g of white powder. A methanol solution of the white powder was allowed to stand to precipitate crystals. 170 mg of plate-like or needle-like crystals of the "F-1028" substance were obtained as hydrochloride.

EXAMPLE 5

An aqueous solution of the hydrochloride of the "F-1028" substance, eluted from the activated carbon column by the procedure as described in Example 4, was passed through a resin column filled with IR-4B[OH⁻]. The solution passed through the column was neutralized with sulfuric acid, concentrated and admixed with ten-fold quantity of ethanol or acetone. There was obtained a sulfate of the "F-1028" substance in powder. The powder was then applied to Sephadex G-10 column to be separated into two fractions. The former was the sulfate, and the latter was the hydrochloride. The latter was again passed through IR-4B[OH⁻] column. The solution passed through the column was neutralized with sulfuric acid to obtain the sulfate. An aqueous solution of the sulfate was concentrated to dryness in vacuo to form a white powder.

The excellent features and marked effects of the active compound of this invention, as an agricultural and horticultural fungicide, can be recognized from the results of the following tests in which it was used against various pathogenic fungi.

EXAMPLE 6

Test on sclerotinia rot of beans and gray mold on vegtables (preventive test):

The hydrochloride of "F-1028" substance of a prescribed concentration was sprayed to bean (variety: *Taisho Kintoki*) in the 2–3 leaf stage at a rate of 15 cc per pot. One day after the spraying, the leaves were cut off, and the hypha growing portion of gray mold fungus and sclerotinia rot fungus which had previously been cultivated in a PDA plate culture medium was punched out in a size of 7 mm in diameter and 2 mm in thickness, and inoculated thereto. The inoculated leaves were placed in a constant-temperature vessel (at 20°C., humidity of more than 98%), and after a lapse of 3 days, the diameters of the enlarged disease spots were measured. Then, the disease spot inhibiting rate was calculated. The results are shown in Table 5 below.

The disease spot inhibiting rate was calculated as follows:

$$\text{Disease spot inhibiting rate (\%)} = \frac{\left(\begin{array}{c}\text{Diameter of disease}\\ \text{spot of untreated leaf}\end{array}\right) - \left(\begin{array}{c}\text{Diameter of disease}\\ \text{spot of treated leaf}\end{array}\right)}{\text{Diameter of disease spot of untreated leaf}} \times 100$$

Table 5

| Compound | Concent-ratio of active ingredient | Gray mold fungus Diameter of disease spot (mm) | Inhibiting rate (%) | Sclerotinia rot fungus Diameter of disease spot (mm) | Inhibiting rate (%) |
|---|---|---|---|---|---|
| F-1028 substance, hydrochloride | 50 ppm | 10 | 67 | 0 | 100 |
|  | 25 ppm | 23 | 23 | 10 | 71 |
| F-1028 substance, culture liquor | Original liquid | 11 | 63 | 0 | 100 |
|  | 8 X | 18 | 40 | 0 | 100 |
| Allisan (50%)* (commercially available, control) | × 1000 (500 ppm) | 10 | 67 | 3 | 91 |
| Polyoxyne (5%) (commercially available, control) | × 1000 (50 ppm) | 19 | 37 | 20 | 57 |
| Non-treated |  | 30 | 0 | 35 | 0 |

*Allisan : 2,6-dichloro-4-nitroaniline.

EXAMPLE 7

Test on gray mold and sclerotinia rot of beans (curative test):

Leaves of bean (variety: *Taisho Kintoki*) were cut off, and gray mold fungus and sclerotinia rot fungus which had been cultivated in a PDA plate culture medium, punched out in a size of 7 mm in diameter and 2 mm in thickness, were inoculated thereto. The inoculated leaves were placed for 24 hours in a humid chamber at 20°C. The diameters of the resultant disease spots were measured.

"F-1028" substance diluted to a prescribed concentration was sprayed to the leaves to an extent such that it trickled from the leaves. The leaves were allowed to dry in air, and again were placed in a constant temperature vessel at 20°C. After a lapse of 48 hours, the diameters of the disease spots were calculated. The degree of progress of the disease spots as against the disease spots before spraying of the chemical was expressed by the disease spot inhibiting rate as follows:

$$\text{Disease spot inhibiting rate (\%)} = \frac{(dc_2 - dc_1) - (dt_2 - dt_1)}{dc_2 - dc_1} \times 100$$

$dc_1$: diameter of the disease spot of non-treated leaf before application of the chemical $dc_2$: diameter of the disease spot of non-treated leaf after application of the chemical $dt_1$: diameter of the disease spot before application of the chemical $dt_2$: diameter of the disease spot after application of the chemical The results obtained are shown in Table 6.

Table 6

| (A) Test results regarding gray mold | | | | |
|---|---|---|---|---|
| Compound | Concentration of active ingredient | Diameter of the disease spot before spraying (mm) | Diameter of the disease spot after spraying (mm) | Disease spot inhibiting rate (%) |
| F-1028 substance | 100 ppm | 14.0 | 16.3 | 81 |
|  | 50 | 14.0 | 17.0 | 75 |
|  | 25 | 14.0 | 19.3 | 59 |
| Allisan (50%) (commercially available, control) | × 1000 (500 ppm) | 12.6 | 18.0 | 43 |
| *Sclex (20%) (commercially available, control) | × 1000 (200 ppm) | 14.0 | 17.7 | 61 |
| Non-treated |  | 11.0 | 23.3 | 0 |

| (B) Test results regarding *sclerotinia rot* | | | | |
|---|---|---|---|---|
| Compound | Concentration of active ingredient | Diameter of the disease spot before spraying (mm) | Diameter of the disease spot after spraying (mm) | Disease spot inhibiting rate (%) |
| F-1028 substance | 100 ppm | 11.3 | 16.3 | 76 |
|  | 50 | 11.3 | 19.6 | 62 |
| Allisan (50%) (commercially available, control) | × 1000 (500 ppm) | 13.6 | 26.6 | 62 |
| Non-treated |  | 12.0 | 33 | 0 |

*Sclex : 3-(3,5-dichlorophenyl)-5,5-dimethyloxazolidinedione-2,4.

EXAMPLE 8

Test on Brown rot (*Sclerotinia cineria*) of peach (field test):

An aqueous solution of the "F-1028" substance with a fixed concentration was sprayed twice with a 7-day interval to peach trees (variety: Kurakata early-ripening, 5th year stage). Both the morbidity upon harvest and morbidity of the fruit packed in a cardbord box for storage at room temperature were investigated. The results are shown in the following table 7.

Table 7

| Sample compound | Test results against Brown rot | | |
|---|---|---|---|
| | Spraying concentration | Morbidity upon harvest | Morbidity after 7 days since packaging in |
| F-1028 substance | 50 ppm | 0 | 0 |
| BENLATE (50%) (commercial, control) | × 1000 | 0.3 | 46.1 |
| SCLEX (20%) (commercial, control) | × 1500 | 0.03 | 7.7 |
| Untreated plot | — | 38.5 | 61.6 |

Remarks:
BENLATE: methyl-1-(butyl carbamoyl)-2-benzimidazole carbamate.
SCLEX: 3-(3,5-dichlorophenyl)-5,5-dimethyloxazolidine dione-2,4.

We claim:

1. The antifungal antibiotic substance "F-1028" having the following formula,

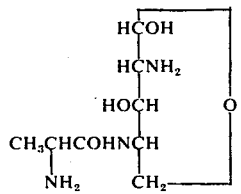

or an hydrochloric acid salt or sulfuric acid salt thereof, which has the following properties (i) –(ix):

i. molecular weight of 219,
ii. colorless crystal
iii. melting point of the hydrochloric acid salt thereof is above 195°C (decomposition),
iv. specific rotation of the hydrochloric acid salt thereof is $[\alpha]_D\ 23 = 63.2°$ (c=1, H$_2$O),
v. UV spectrum of an aqueous solution of the hydrochloric acid salt thereof has no peculiar absorption as shown in FIG. 1,
vi. IR spectrum of a mixture of the hydrochloric acid salt thereof with potassium bromide is as shown in FIG. 2,
vii. Rf value in thin-layer chromatography with silica gel is 0.68 with a developing solvent consisting of n-propanol-pyridine-acetic acid-water in a ratio of 15:10:3:12; and 0.21 with a developing solvent consisting of butanol-acetic acid-water in a ratio of 3:1:2,
viii. readily soluble in water and insoluble in chloroform, benzene and ether, and
ix. color reaction is positive with ninhydrin, Ehrlich, Elson-Morgan, Tollens and Benedict reagents, and negative with Molisch, Sakaguchi, maltol and ferric chloride reagents.

2. The antifungal antibiotic substance of claim 1 wherein the acid salt is the hydrochloric acid salt.

* * * * *

UNITED STATES PATENT AND TRADEMARK OFFICE
CERTIFICATE OF CORRECTION

PATENT NO. : 3,956,276
DATED : May 11, 1976
INVENTOR(S) : Toju Hata et al

It is certified that error appears in the above–identified patent and that said Letters Patent are hereby corrected as shown below:

Item 73, line 1, delete "Moyaku", insert -- Noyaku --

Item 73, line 2, delete "Kiyasato", insert -- Kitasato --

Signed and Sealed this

Third Day of August 1976

[SEAL]

Attest:

RUTH C. MASON
*Attesting Officer*

C. MARSHALL DANN
*Commissioner of Patents and Trademarks*